United States Patent [19]

Ogi

[11] Patent Number: 4,650,327
[45] Date of Patent: Mar. 17, 1987

[54] OPTICAL CATHETER CALIBRATING ASSEMBLY

[75] Inventor: Darrell H. Ogi, Sunnyvale, Calif.

[73] Assignee: Oximetrix, Inc., Mountain View, Calif.

[21] Appl. No.: 791,706

[22] Filed: Oct. 28, 1985

[51] Int. Cl.[4] .................................................. G01J 1/02
[52] U.S. Cl. ...................................... 356/243; 356/41; 356/42
[58] Field of Search ........................ 356/39, 40, 41, 42, 356/243; 250/252.1; 128/632, 633, 634

[56] References Cited

U.S. PATENT DOCUMENTS 4,322,164  3/1982  Shaw et al. .......................... 356/243

Primary Examiner—Eugene R. LaRoche
Assistant Examiner—Robert J. Pascal
Attorney, Agent, or Firm—Martin L. Katz; Robert W. Stevenson; Robert S. Kelly

[57] ABSTRACT

A calibrating device for an optical catheter is provided in order to calibrate the catheter for use in a catheter oximeter system. The calibrating device includes a tube having a reference block therein which is spring-loaded into compliant engagement with the distal end of the catheter carrying the fiberoptic light transmitting and receiving guides. A releasable strap tightly secures the catheter to the calibrating device. The packaged catheter is therefore ready for calibration by simply removing the proximal end thereof from a sealed package while the calibrating device and major length of the catheter remain in their sealed and sterilized condition and connecting it to a processor for performing the calibration operation.

15 Claims, 6 Drawing Figures

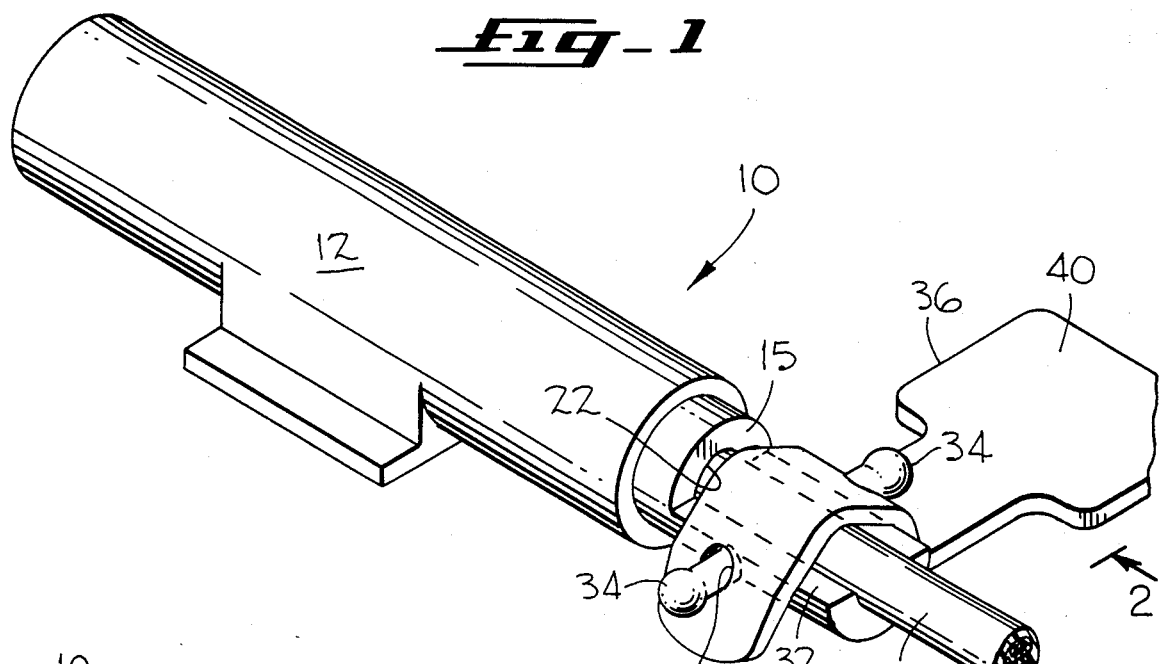
*fig_1*
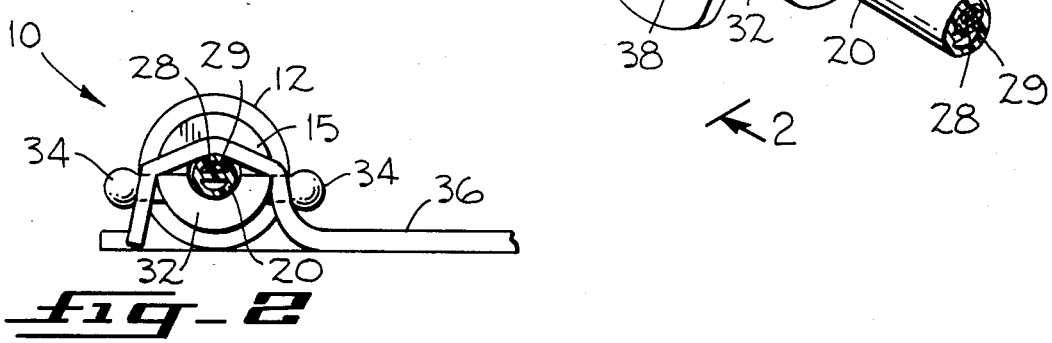
*fig_2*
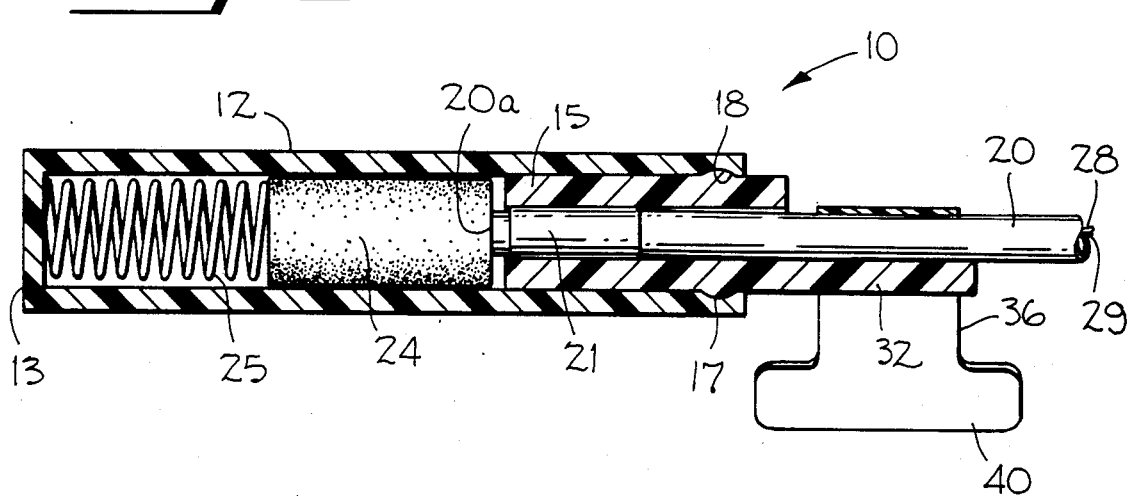
*fig_3*

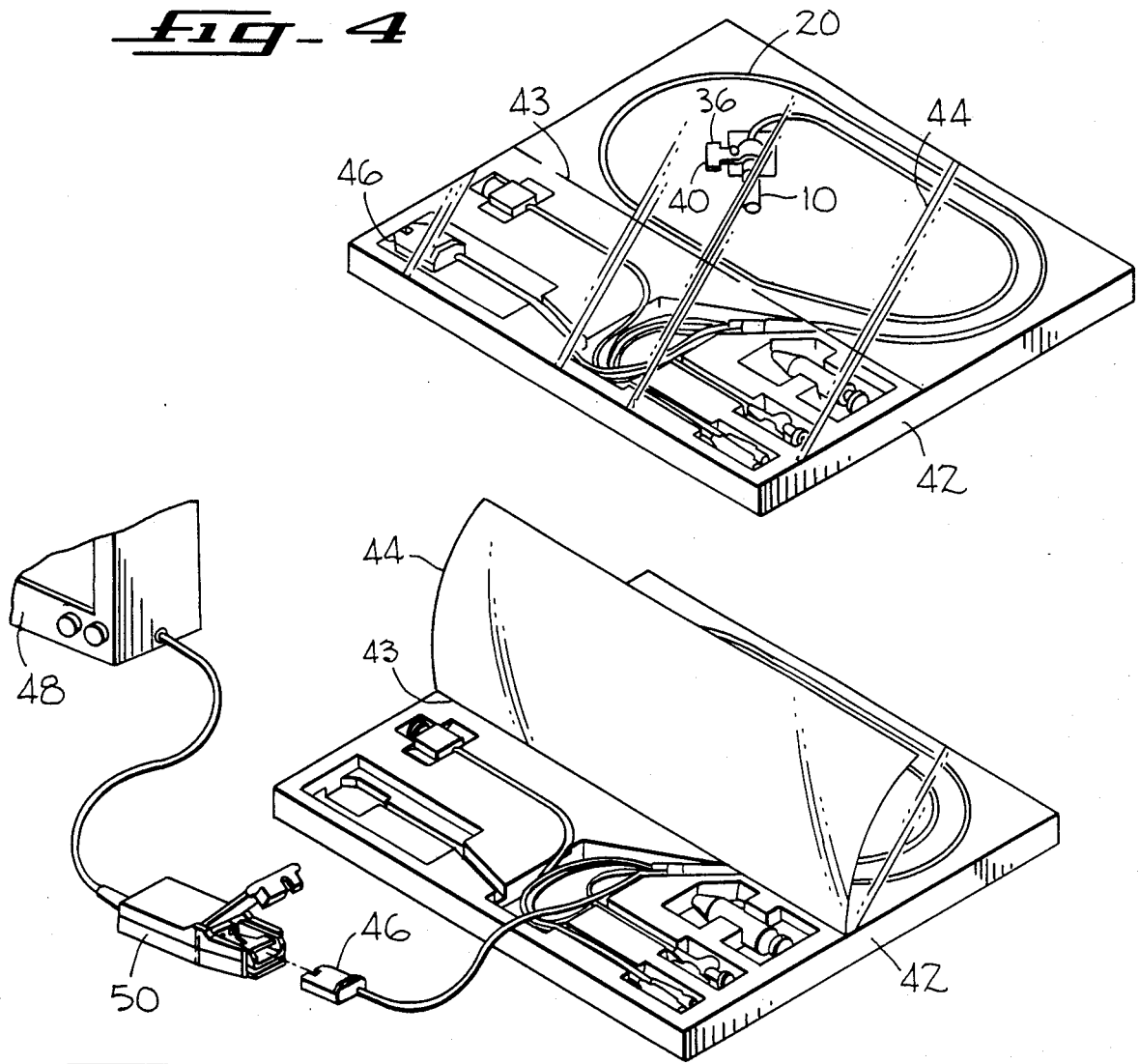
fig_4
fig_5
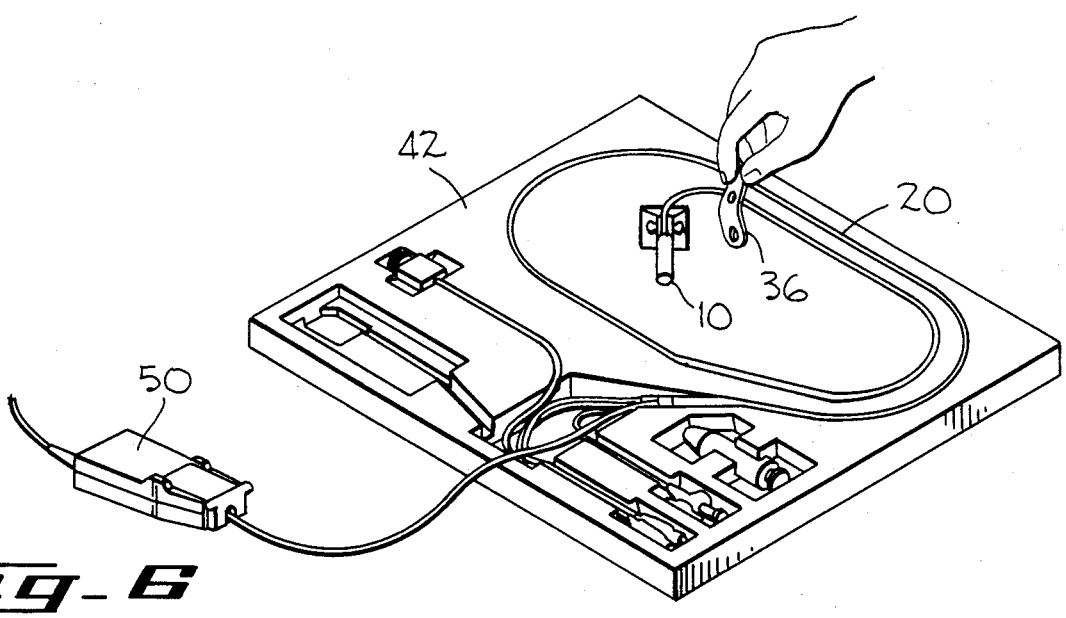
fig_6

OPTICAL CATHETER CALIBRATING ASSEMBLY

BACKGROUND OF THE INVENTION

1. Field of the Invention

This invention relates to a calibration device and calibrating system for optical catheters used in a catheter oximetry system, and more particularly, it relates to a calibrating device which may remain with the sealed and sterilized distal end of the catheter within a package while the proximal end of the catheter is plugged into a computer or processor in order to perform the calibrating operation.

2. Description of the Prior Art

A catheter oximetry system provides accurate, continuous, real-time measurement of mixed venous oxygen saturation using multiple wavelength reflection spectrophotometry. The color of red blood cells progressively changes from scarlet to purple as the amount of oxygen the red blood cells are carrying decreases. When light of different selected wavelengths illuminates the blood, the amount of light backscattered, or reflected, at each wavelength depends upon the color, and therefore, oxygen level of the blood. Careful choice of wavelengths in the transmittal light allows accurate measurement of oxygenated hemoglobin with minimal interference by other blood characteristics such as temperature, pH, and hematocrit.

Approximately 98% of the oxygen in the blood is chemically combined with hemoglobin in red blood cells. The absorption of red and infrared light substantially differs for oxygenated and deoxygenated hemoglobin, and it varies for different wavelengths of light within this red/infrared spectrum. Therefore, the relative amounts of oxygenated hemoglobin and deoxygenated hemoglobin in the blood can be determined by measuring the relative absorption of light at different selected wavelengths. The percentage of hemoglobin which is in the oxygenated form is defined as the oxygen saturation of the blood in the equation:

$$\text{Oxygen Saturation} = \frac{HbO_2}{Hb + HbO_2} \times 100$$

where $HbO_2$ is the oxygenated hemoglobin concentration and $Hb$ is the deoxygenated hemoglobin concentration.

A widely used catheter oximetry system consists of three basic components: (1) a disposable fiberoptic pulmonary artery catheter that has a distal end adapted to be inserted into a vein of a patient and that interfaces at its other end with (2) an optical module containing light emitting diodes, a photodetector and associated electronics, which in turn, interfaces with the electrical leads of (3) a computer-based instrument that performs all of the data processing and control functions with displays, alarms and associated read-out devices. The instrument and optical module may be reused many times with different patients, but the catheter is used only with a single patient during a single operation or monitoring process. Thus, the catheters are disposable and are arranged to be separately packaged in sealed aseptic packages each with a specially designed optical connector plug adapted to be plugged into the optical module when the catheter is ready for use.

Since the total amount of light reflected back from the blood under test during the catheter oximetry measurements is relatively low, and since variations in the manufacturing of the optical components (particularly the fiberoptics) create differences in transmission which affect the output readings, it is important that each catheter be separately calibrated immediately before it is used so as to relate the actual light intensities received from the sample under test to the unknown concentrations of the substances being quantified in the sample under test. This may be accomplished by initially measuring a given sample of blood with the catheter and then wholly independently measuring the same blood in the laboratory by a different technique in order to match the laboratory calculated actual oxygen saturation content with the instrument calculated content and adjusting the latter accordingly. Such a technique has the obvious disadvantage, however, that the time required for making the laboratory tests causes an undesirable delay between the time of catheter placement and the time at which the oxygen saturation measurements can be utilized with assurance of their correctness. In order to overcome this obvious disadvantage, various techniques have been proposed whereby the catheter is initially calibrated using a reference material such as suspensions of milk of magnesia combined with dyes or filters of various light reflective targets which the distal end of the catheter can be initially directed to and which have known reflectivity characteristics.

One method of initial catheter calibration which has found wide acceptance in the field is disclosed in U.S. Pat. No. 4,322,164 to Robert F. Shaw et al. Briefly, this method involves a reference block formed as a solid compliant mass having a plurality of light reflective particles embedded therein. This reference block is received within an enclosed tube, and, in the initial packaging of the catheter, the distal end thereof is inserted into the tube adjacent to but spaced from the reference block and gripped to restrain further movement. The reference block is then spring loaded but restrained by a releasable catch so that it can be released into resilient engagement with the end of the catheter at the time that the calibration measurements are made. Once the calibration readings have been obtained, the catheter can be pulled loose from the tube and reference block and placed in a patient for obtaining blood oxygen saturation measurements in the manner intended. The initial calibration readings are obtained with the reference block and catheter remaining in the package in a sealed and sterilized condition while the connector plug end of the catheter is connected to the optical module and oximetry processor.

While the aforedescribed catheter calibration scheme has met with considerable success, there have been some problems from time to time. Thus, it may be inconvenient for the doctor or nurse to perform the separate operation of releasing the reference block into engagement with the catheter tip, or, such operation may fail or expose the catheter to possible contamination prior to its actual time of use.

SUMMARY OF THE INVENTION

With the optical catheter assembly package of the present invention, a catheter having transmitting and receiving light guides therein is arranged to be packaged in a tray with the distal end of the catheter being received in a calibrating device. The calibrating device includes a tubular enclosure within which a reference element is urged into compliant engagement with the distal end of the catheter and with means being provided for tightly gripping and holding the catheter to the enclosure so that the catheter and calibrating device are ready for an immediate calibration operation in the package without any additional movement of either catheter or reference block being required.

The package is sealed with a cover material that encloses the catheter and calibrating device in the tray in a sealed and sterile condition. When the catheter is ready for use, a portion of the sealing material can be removed while the remainder is left in its sealed and sterile condition so as to only expose the optical connector at the proximal end of the catheter permitting it to be connected to an oximetry system to provide a calibration reading for the catheter—all while the distal end and insertable major length of the catheter remains in a sealed, sterile condition. Upon the conclusion of the calibration process and the recording of the results within the oximetry system, the remainder of the sealing material can be removed, the calibrating device readily removed from the distal end of the catheter, and the catheter placed directly in the patient for continuous blood oxygen saturation readings.

BRIEF DESCRIPTION OF THE DRAWINGS

FIG. 1 is an isometric view of the calibrating device of the present invention with the distal end of an oximetry catheter being shown inserted and clamped therein.

FIG. 2 is an enlarged section taken along line 2—2 of FIG. 1.

FIG. 3 is an enlarged longitudinal section through the calibrating device and catheter of FIG. 1.

FIGS. 4-6 are schematic views illustrating the packaging of the catheter and calibrating device of the present invention and particularly showing the manner in which the calibrating operation is carried out.

DESCRIPTION OF THE PREFERRED EMBODIMENT

The calibrating device 10 of the present invention is shown in FIGS. 1-3 wherein it will be seen to be comprised of a cylinder 12 which is closed at one end 13 and open at the other end thereof (FIG. 3). Received within the open end of the cylinder 12 is a plug 15 which is provided near the center thereof with a circumferentially extending rib 17 adapted to be received within a detent 18 just within the open end of the cylinder 12. The plug is inserted in the cylinder during the assembly of the calibrating device, and, as indicated in FIG. 3, it is snapped into snug engagement therewith.

The distal end of an optical catheter 20 is adapted to be inserted through the plug 15 within an axial passage 22 extending therethrough. As seen in FIG. 3, the axial passage 22 is just slightly larger than the outer diameter of the catheter and its balloon 21 so as to snugly confine the catheter therewithin. Positioned within the inner end of the tubular member 12 is a reference block 24 and a coil spring 25 with the spring urging the reference block into firm engagement with the flat distal end 20a of the catheter 20 at a position spaced inwardly from the end of the plug 15.

The reference block 24 is the same as that shown and described in the aforementioned prior U.S. Pat. No. 4,322,164 to Robert F. Shaw et al. Briefly, the reference block comprises a solid cylindrical element formed of a silicone resin and having a plurality of tiny particles scattered throughout its mass to provide scattering and reflecting surfaces for the light beams transmitted by the catheter 20. The particles will typically have dimensions within the range of from about 0.02 to about 20 microns and should be uniformly dispersed within the solid mass of the reference block 24. The mass is translucent in nature and has compliant characteristics at the surface thereof so that it will yield when pressed against the rigid surface 20a of the catheter thereby insuring a snug fit which will not become easily dislodged during handling of the catheter and attached calibrating device.

As shown in FIGS. 1-3 the catheter 20 comprises a conventional optical catheter useful in oximetry measurements having a pair of separated lumens with a transmitting light guide 28 formed of a single fiber and a receiving light guide 29 likewise formed of a single fiber extending side-by-side along the length of the catheter to an exposed position at the flattened surface 20a at the very end of the catheter. Light carried along the transmitting fiber 28 is directed into the reference block 24 where it is backscattered and a portion thereof is reflected back into the receiving fiber 29 for transmission back to the oximetry processing apparatus to provide readings useful for calibrating the catheter and associated optical components.

Since it is critical that the catheter remain in snug engagement with the compliant reference block from the time that it is initially packaged up until and through the time when the calibration readings are obtained, means are provided for insuring that this condition will be maintained. Thus, it will be seen that the outer end of the plug 15 is removed so as to provide a short axially extending section 32 which exposes the longitudinally extending passage 22 through the plug. A pair of prongs 34 are provided at opposed sides of the section 32 of the plug and extend outwardly therefrom. A strap 36 formed of a highly resilient and elastomeric material is stretched between the prongs 34 so as to tightly engage one side of the catheter 20 and force it into tight engagement with the longitudinally exposed section of the passage 22 wherein it will remain until the strap is removed. This is accomplished by providing a pair of apertures 38 (one only being shown in FIG. 1) at one end of the strap which apertures are spaced apart by a distance less than the distance between the prongs 34. One aperture is then forced over one of the prongs 34 and the strap is stretched until the other aperture can be received upon the opposed prong 34. Also, as shown, the strap includes an enlarged tab 40 at the outwardly projecting end thereof which tab is of a size whereby it can be readily gripped between the fibers in order to pull the strap loose from the prongs at the conclusion of the calibration operation in order to release the catheter from the calibrating device.

The use of the calibrating device 10 of the present invention in a catheter oximetry system is shown sequentially in FIGS. 4, 5 and 6. With reference to FIG. 4, it will be seen that the catheter 20 is arranged to be packaged within conforming recesses set in a rectangularly shaped plastic tray 42. A piece of plastic sealing material 44 is laid atop the tray and sealed thereto, and the tray and enclosed catheter are then sterilized using conventional sterilization techniques. The distal end of the catheter is connected directly to the calibrating device 10 in the aforedescribed manner and clamped thereto by the strap 36 with the tab 40 of the strap extending to the side in a position adapting it to ready removability. The proximal end of the catheter includes the optical connector plug 46 and a plurality of other conventional output connections including lumen connections for pressure readings, samplings, or infusion, a thermistor connection for cardiac outputs and a mechanism connected to pressurize the balloon 21 at the tip of the catheter—all of such elements being conventional with the details thereof having no relevance with respect to the present invention.

As shown in FIG. 5, the first step in the calibration operation is to remove the plastic sealing material 44 from atop the tray to allow the fiberoptic connector plug 46 to be removed and coupled to the computer or processor 48. As can be seen, however, the sealing material 44 is provided with two sections separated by a seam or scoreline 43 whereby only one portion thereof is removed during the initial peeling of the material, as shown in FIG. 5, exposing only the proximal end of the catheter and the connections thereto (including the connector plug 46) but leaving the main body of the catheter, which will later be placed in the patient, within the package in its original sealed and sterilized condition. The connector plug can then be placed in a receptacle in an optical module 50 which provides the electro-optical coupling between the connector plug 44 and the processing circuitry of the computer 48. When this is accomplished, the computer is turned on to provide signals to the optical module 50 creating the light sources which are directed via the coupling 46 down the length of the catheter to the reference block 24 wherein the light is backscattered and reflected back to the optical module. The module then converts these light signals into electrical signals for processing by the computer. In this way the appropriate calibration readings are obtained and stored in the computer.

Once the relevant calibration readings have been obtained the catheter is calibrated and immediately ready for use in monitoring the blood oxygenation of a patient. As shown in FIG. 6, the remainder of the sealing material 44 is then removed, and a simple pulling away of the strap 36 from its secured position on the calibrating device 10 leaves the catheter 20 free from its locked engagement therewith. The nurse or doctor can then directly take the catheter and place it in the patient.

It will be seen that the calibrating device of the present invention permits the catheter to be directly locked to a calibrating device and packaged in such manner so that no additional steps are required other than to connect the proximal end of the catheter to suitable processing circuitry in order to obtain appropriate calibration readings. Once the readings have been obtained, the catheter is ready for immediate use, and the protective and sealing material can be removed to permit the catheter to be immediately used. It has been found that the packaging method as aforedescribed will stand up under repeated jostling or dropping without dislodging the reference block from the catheter.

Although the best mode contemplated for carrying out the present invention has been herein shown and described, it will be apparent that modification and variation can be made without departing from what is regarded to be the subject matter of the invention.

What is claimed is:

1. A calibrating device for use with an optical oximetry catheter comprising a tubular enclosure having a passage therein for reception of the distal end of the catheter, a solid reference element for receiving a light beam from a transmitting light guide in said catheter and for scattering and reflecting light back to a receiving light guide in said catheter in a manner similar to that of blood, said reference element being received within the passage in said enclosure and having a compliant surface characteristic, means for urging said reference element into compliant engagement with the distal end of said catheter, and a resilient strap stretched across the entrance of said passage and removably fastened to the enclosure so as to provide a gripping force on said catheter to prevent movement thereof with respect to the enclosure.

2. A calibrating device according to claim 1 wherein said tubular enclosure is comprised of a tubular member having a closed end and an open end and a plug received within the open end of the tubular member, said reference element and said means for urging being received within the tubular member, said plug having a narrow axial passage therethrough for receiving the catheter in close confining engagement, the reference element being urged into engagement with the end of the catheter at a position spaced from the inner end of the plug within the tubular member.

3. A calibrating device according to claim 2 wherein said axial passage in the plug is longitudinally exposed for a short distance at the outer end of the plug positioned outside of said tubular member, said strap being releasably mounted upon said plug within the longitudinally exposed axial passage section thereof so as to clamp the catheter to the plug.

4. A calibrating device according to claim 3 including a pair of prongs extending laterally at opposed sides of the longitudinally exposed axial passage section of the plug, said strap having a pair of spaced apertures adapted to be received by said prongs when the strap is stretched therebetween to clamp the catheter to the plug.

5. A calibrating device according to claim 4 wherein said strap includes an enlarged tab spaced from the tubular enclosure for permitting the strap to be gripped and readily removed.

6. An optical catheter assembly ready for use in a catheter oximetry system, said assembly comprising an optical catheter having at least a pair of light guides therein extending to the distal end thereof with one of said guides adapted to transmit light to the distal end of the catheter and with the other of said guides adapted to receive light reflected back from the material at said distal end, and a calibrating device attached to said distal end of the catheter for providing an initial calibration reading for the catheter, said calibrating device comprising a tubular enclosure having a passage therein for reception of the distal end of the catheter, a solid reference element for receiving a light beam from the transmitting light guide in said catheter and for scattering and reflecting light back to the receiving light guide in said catheter in a manner similar to that of blood, said reference element being received within the passage in said enclosure and having a compliant surface characteristic, means for urging said reference element into compliant engagement with the distal end of said catheter, and a resilient strap stretched across the entrance of said passage and removably fastened to the enclosure so as to provide a gripping force on said catheter to prevent movement thereof with respect to the enclosure and reference element therein.

7. An optical catheter assembly according to claim 6 wherein said passage in the tubular enclosure is relatively narrow at the end of the passage in which the catheter is inserted for close confinement of the catheter and wherein said passage is relatively wide in the inner portion of the tubular enclosure for securing said reference element.

8. An optical catheter assembly according to claim 7 wherein said axial passage is longitudinally exposed for a short distance at the outer end of the tubular enclosure, said strap being releasably mounted upon the longitudinally exposed axial passage section of the enclosure so as to clamp the catheter thereto.

9. An optical catheter assembly according to claim 8 including a pair of prongs extending laterally at opposed sides of the longitudinally exposed axial passage section of the enclosure, said strap having a pair of spaced apertures adapted to be received by said prongs when the strap is stretched therebetween to clamp the catheter to the enclosure.

10. An optical catheter assembly according to claim 9 wherein said strap includes an enlarged tab spaced from the tubular enclosure for permitting the strap to be gripped and readily removed.

11. An optical catheter assembly according to claim 6 including a pair of prongs extending laterally at opposed sides of the entrance of the enclosure, said strap having a pair of spaced apertures adapted to be received by said prongs when the strap is stretched therebetween to clamp the catheter to the enclosure.

12. An optical catheter assembly according to claim 11 wherein said strap includes an enlarged tab spaced from the tubular enclosure for permitting the strap to be gripped and readily removed.

13. An optical catheter assembly package providing a sealed and sterilized catheter ready for use in a catheter oximetry system, said package comprising a tray; an optical catheter having at least a pair of light guides therein extending from an optical connector at one end thereof throughout the length of the catheter to the distal end thereof with one of said guides adapted to transmit light to the distal end of the catheter and with the other of said guides adapted to receive light reflected back from the material at said distal end, said catheter being received in said tray; a calibrating device attached to said distal end of the catheter for providing an initial calibration reading for the catheter, said calibrating device comprising a tubular enclosure having a passage therein for reception of the distal end of the catheter, a solid reference element for receiving a light beam from the transmitting light guide in said catheter and for scattering and reflecting light back to the receiving light guide in said catheter in a manner similar to that of blood, said reference element being received within the passage in said enclosure and having a compliant surface characteristic, means for urging said reference element into compliant engagement with the distal end of said catheter, and means removably fastened to the enclosure for providing a gripping force on said catheter to prevent movement thereof with respect to the enclosure and reference element therein; and a flexible sealing material covering and enclosing the catheter and calibrating device in the tray in a sealed and sterile condition, a portion of said sealing material being removable while the remainder of the sealing material remains in its sealed and enclosing condition to expose the optical connector of the catheter thereby permitting it to be connected to an oximetry system to provide a calibration reading for the catheter based on the reflected light received from the reference element.

14. An optical catheter assembly package according to claim 13 including a pair of prongs extending laterally at opposed sides of the entrance of the enclosure, said means for providing a gripping force comprising a strap having a pair of spaced apertures adapted to be received by said prongs when the strap is stretched therebetween to clamp the catheter to the enclosure.

15. An optical catheter assembly according to claim 14 wherein said strap includes an enlarged tab spaced from the tubular enclosure for permitting the strap to be gripped and readily removed and the catheter to be thereafter removed from the tray after the calibration readings are obtained.

* * * * *